United States Patent [19]

Vagt et al.

[11] Patent Number: 4,730,040

[45] Date of Patent: Mar. 8, 1988

[54] PREPARATION OF CAPROLACTAM

[75] Inventors: Uwe Vagt, Speyer; Rolf Fischer, Heidelberg; Franz Merger, Frankenthal; Hans-Martin Hutmacher, Ludwigshafen, all of Fed. Rep. of Germany

[73] Assignee: BASF Aktiengesellschaft, Ludwigshafen, Fed. Rep. of Germany

[21] Appl. No.: 7,788

[22] Filed: Jan. 28, 1987

[30] Foreign Application Priority Data

Jan. 28, 1986 [DE] Fed. Rep. of Germany ....... 3602377

[51] Int. Cl.⁴ ............................................. C07D 201/08
[52] U.S. Cl. ................................................... 540/538
[58] Field of Search ........................................ 540/538

[56] References Cited

U.S. PATENT DOCUMENTS 3,485,821  12/1969  Sheehan ............................... 540/538

FOREIGN PATENT DOCUMENTS 0031100  7/1981  Eurpoean Pat. Off. ............ 560/177
0091091  10/1983  European Pat. Off. ............ 562/577
1191539  5/1970  United Kingdom ................ 540/538

OTHER PUBLICATIONS

Journal of the American Chemical Society, vol. 64, pp. 1416–1421 (1942).

Primary Examiner—Robert T. Bond
Attorney, Agent, or Firm—Keil & Weinkauf

[57] ABSTRACT

ε-caprolactam is prepared by a process in which
(a) a 5-formylvalerate is reacted with water in the presence of an acidic agent at from 30° to 200° C.,
(b) the 5-formylvaleric acid thus obtained is reacted with excess ammonia and hydrogen in the presence of a hydrogenation catalyst and of a solvent which is inert under the reaction conditions, at from 50° to 150° C. under superatmospheric pressure, and
(c) after the ammonia has been separated off, the resulting solution of 6-aminocaproic acid is heated to 150°–370° C. and the caprolactam formed is isolated.

9 Claims, No Drawings

PREPARATION OF CAPROLACTAM

The present invention relates to a process for the preparation of caprolactam from 5-formylvalerates.

In a process described in J. Amer. Chem. Soc. 64 (1942), 1416 et seq., 5-formylvaleric acid is obtained by reacting 2-hydroxycyclohexanone with lead tetraacetate in glacial acetic acid. This process has the disadvantage that it requires expensive starting materials and gives inadequate yields. It also has the disadvantage that the lead compounds inevitably produced have to be disposed of. In another process, described in Chem. Ber. 72 (1939), 1194 et seq., 5-formylvaleric acid is obtained by reacting cyclohexanone with alkaline hydrogen peroxide. However, this process gives only poor selectivities and requires long reaction times. In another process, described in European Patent Application No. 91,091, 5-formylvaleric acid is prepared by oxidizing cyclohexanone with molecular oxygen in the presence of homogeneous catalysts, e.g. iron(III) chloride and thiourea. In this process, however, adequate selectivities are obtained only at conversions of less than 50%. Moreover, the catalysts which are present in the form of a homogeneous solution have to be separated off from the reaction mixture, and this is expensive.

Japanese Patent Publication 21 138/66 furthermore discloses a process in which 5-formylvaleric acid, ammonia and water as a diluent are reacted in the presence of hydrogen and of a hydrogenation catalyst at above 100° C. to give caprolactam. However, the yields of caprolactam are only 20-40%. It has also been disclosed that caprolactam can be prepared by first treating a mixture of 6-hydroxycaproic acid, adipic acid, 5-formylvaleric acid and other carboxylic acids with hydrogen at 200°-300° C. in the presence of ammonia and a hydrogenation catalyst, and then cooling the mixture, separating off ammonium salts of 5-cyanovaleric acid and of adipic acid monoamide, adding further ammonia and water and heating the reaction mixture to 300°-400° C. (Japanese Patent No. 31,538 (1971)). The process does not appear very advantageous since it involves a large number of steps, making it expensive, and gives poor selectivities. The reaction of gaseous 5-formylvaleric acid (2% by volume) with ammonia (8% by volume), hydrogen (50% by volume) and steam (40% by volume) at 280° C. under atmospheric pressure in the presence of copper oxide, chromium oxide and manganese oxide to give caprolactam has also been described (GB No. 1,191,539). Because of the relatively low space-time yield and the problems with catalyst deactivation which arise as a result of the very short experimental times (6 h) mentioned in the examples, the process appears uneconomical.

Finally, it is known that 6-aminocaproic acid, dissolved in water (U.S. Pat. No. 3,485,821) or alcohols (U.S. Pat. No 3,506,148) can be cyclized at from 150° to 350° C. and at from 170° to 200° C., respectively, to give caprolactam.

It is an object of the present invention to provide a process for the preparation of caprolactam from 5-formylvalerates, the said process giving high yields and producing only a small amount of by-products.

We have found that this object is achieved by a process for the preparation of caprolactam, wherein (a) a 5-formylvalerate is reacted with water in the presence of an acidic agent at from 30° to 200° C., (b) the 5-formylvaleric acid thus obtained is reacted with excess ammonia and hydrogen in the presence of a hydrogenation catalyst and of a solvent which is inert under the reaction conditions, at from 50° to 150° C. under superatmospheric pressure, and (c) after the ammonia has been separated off, the resulting solution of 6-aminocaproic acid is heated to 150°-370° C., in particular 250°-330° C., and the caprolactam formed is isolated.

The novel process has the advantages that it permits the preparation of caprolactam in a simple manner and in high yields from 5-formylvalerates, takes place in a short time and produces a small amount of by-products, and catalysts which can readily be separated off are used. The novel catalyst is noteworthy in that 5-formylvaleric acid was expected to undergo intermolecular or intramolecular aldol condensation (formation of five-membered rings) in an acidic medium. For example, Houben-Weyl, Methoden der organischen Chemie, Volume VII/1, page 87, discloses that adipodialdehyde in an acidic medium undergoes an intramolecular aldol condensation with formation of cyclopentenecarbaldehyde.

Preferred 5-formylvalerates are derived from alkanols of 1 to 12 carbon atoms, cycloalkanols of 5 to 7 carbon atoms, aralkanols of 7 or 8 carbon atoms or phenols of 6 to 8 carbon atoms. Particularly preferred starting materials are $C_1$–$C_4$-alkyl 5-formyl-valerates. Examples of suitable starting materials are methyl 5-formylvalerate, ethyl 5-formylvalerate, n-propyl 5-formylvalerate, isopropyl 5-formylvalerate, n-butyl 5-formylvalerate, 2-ethylhexyl 5-formylvalerate, cyclohexyl 5-formylvalerate and phenyl 5-formylvalerate. Methyl 5-formylvalerate has become particularly important industrially. 5-formylvalerates are readily obtainable by hydroformylation of 4-pentenoates by the process described in European Patent Application No. 31,100.

In general, from 1 to 200, in particular from 50 to 150, moles of water are employed per mole of 5-formylvalerate. Moreover, inert solvents which are liquid under the reaction conditions may be concomitantly used. Examples of suitable solvents are hydrocarbons, such as cyclohexane or toluene, halohydrocarbons, such as dichloromethane or tetrachloromethane, and ethers, such as dioxane or diglyme. Where solvents are used, the 5-formylvalerate is employed in the form of a 1-90, in particular 5-20, % strength by weight solution.

The reaction is carried out at from 30° to 200° C., advantageously at from 50° to 120° C. In general, the reaction is carried out under atmospheric pressure, although it is also possible to use slightly reduced pressure or slightly superatmospheric pressure, e.g. up to 20 bar.

The reaction is carried out in the presence of an acidic agent. Examples of suitable acidic agents are sulfonic acids, such as toluene sulfonic acid, Lewis acids, such as boron trifluoride or zinc chloride, nonoxidizing mineral acids, such as sulfuric acid, hydrochloric acid or hydrobromic acid, lower fatty acids, e.g. lower aliphatic carboxylic acids, such as formic acid, acetic acid or propionic acid, and highly acidic cation exchangers. Highly acidic cation exchangers of this type consist of, for example, crosslinked polystyrene possessing sulfo groups, phenol resins possessing sulfo groups or acidic zeolites.

Sulfonic acids, Lewis acids or nonoxidizing mineral acids are advantageously used in catalytic amounts, for example from 0.002 to 0.25 mole per mole of 5-formylvalerate. Aliphatic carboxylic acids are generally employed in amounts of from 0.1 to 1 mole per mole of 5-formylvalerate. Strongly acidic cation exchangers are particularly preferably used.

The process can be carried out batchwise or, advantageously, continuously, for example in a stirred kettle cascade. It is advantageous for the alcohol produced during the hydrolysis to be removed continuously from the reaction mixture by distillation. Where strongly acidic cation exchangers are used, it is advantageous to carry out the reaction in such a way that the said cation exchanger is arranged as a fixed bed, for example in a tube reactor, and the reaction mixture is passed over the said catalyst by the trickle bed procedure. In a particularly advantageous embodiment, the reaction mixture is first passed, by the trickle bed procedure, through a first reaction zone containing a strongly acidic fixed bed cation exchanger, and then circulated over a strongly acidic fixed bed cation exchanger in a second reaction zone, and is removed at the rate at which it is fed to the first reaction zone. Advantageously, unconverted 5-formylvalerate is extracted from the resulting reaction mixture, for example with hydrocarbons which are inert and liquid under the reaction conditions, such as cyclohexane, and is advantageously reused.

In another advantageous procedure, the 5-formylvalerate and water in excess are passed through a column charged with a strongly acidic cation exchanger, alcohols are distilled off at the upper end and an aqueous solution of 5-formylvalerate is removed at the lower end.

5-formylvaleric acid can be removed from the resulting aqueous solution in pure form by distillation. The aqueous solution of 5-formylvaleric acid, which contains the latter in an amount of, for example, from 3 to 15% by weight, is advantageously used directly for the preparation of 6-aminocaproic acid. In a second stage (stage b), the resulting 5-formylvaleric acid is then reacted with excess ammonia and hydrogen in the presence of a hydrogenation catalyst and of a solvent at from 50° to 150° C. under superatmospheric pressure.

5-formylvaleric acid is used in general as a 1-50, preferably 2-35, in particular 5-25, % strength by weight solution. The solutions predominantly contain monomers and a small amount of low molecular weight oligomeric 5-formylvaleric acid. Examples of suitable solvents which are inert under the reaction conditions are water, monohydric or polyhydric alcohols of 1 to 5 carbon atoms, ethers, such as dioxane, tetrahydrofuran or diglyme, and mixtures of the stated solvents. Water is preferably used as the solvent. In particular, it has proven useful to employ aqueous solutions of 5-formylvaleric acid as obtained in stage a.

As a rule, from 2 to 50, in particular from 4 to 30, moles of ammonia are used per mole of 5-formylvaleric acid.

The reaction is carried out at from 50° to 150° C., advantageously from 70° to 130° C., in general under from 10 to 400, advantageously from 20 to 300, in particular from 50 to 250, bar. As a rule, hydrogen is employed in a ratio of from 1 to 10 moles per mole of 5-formylvaleric acid. Hydrogen is preferably used in excess, for example from 2 to 5 moles of hydrogen are employed per mole of 5-formylvaleric acid.

Suitable hydrogenation catalysts are metals of group 8 of the periodic table, such as nickel catalysts, cobalt catalysts or noble metal catalysts, such as ruthenium, platinum or palladium. The catalysts may contain activating additives, such as zirconium, manganese, copper or chromium, and may be used in the form of solid catalysts or deposited on carriers, such as alumina, silica gel, clay or active carbon. Skeleton catalysts are also suitable.

Suitable catalysts contain, for example, from 80 to 100% by weight, based on the metal content of the catalyst, of cobalt and/or nickel. In addition to cobalt and/or nickel, the catalysts may contain metals such as copper or chromium, for example in an amount of up to 20% by weight, based on the metal content. The catalysts can be applied on carriers, for example silica gel, magnesium silicate, aluminum phosphate, boron phosphate, alumina or active carbon. The metal content of the supported catalysts is advantageously from 5 to 80% by weight, based on the total catalyst material.

Other suitable catalysts are those which are prepared by calcining compounds of the formula I $[Mg_aNi(II)_b\text{-}Co(II)_c Al_2]CO_3(OH)_{16} \cdot 4 H_2O$, where a is an integer or decimal number from 0 to 4 and b and c are each an integer or decimal number from 0 to 6, with the proviso that $2(a+b+c)=12$, at from 200° to 600° C. and then reducing the product with hydrogen at elevated temperatures. The following compounds of the formula I are preferably used as starting materials:

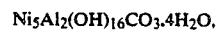

$Ni_5Al_2(OH)_{16}CO_3 \cdot 4H_2O$,

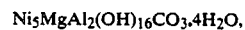

$Ni_5MgAl_2(OH)_{16}CO_3 \cdot 4H_2O$,

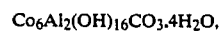

$Co_6Al_2(OH)_{16}CO_3 \cdot 4H_2O$,

$Co_5MgAl_2(OH)_{16}CO_3 \cdot 4H_2O$.

The compounds of the formula I are obtained, for example, as follows: nickel, aluminum, cobalt and magnesium in the form of their water-soluble salts, such as chlorides, sulfates or, preferably, nitrates, are dissolved together in water in a ratio which very closely approaches the desired composition of the catalyst and corresponds to the formula I in its stoichiometry.

The overall molarity of the metal salt solution in respect of metal ions should be about 0.5-3, preferably 1.0-2. The metal salt solution is heated to 50°-100° C., preferably 80°-100° C., and combined, in the course of from 0.5 to 10, preferably from 1 to 3, minutes, with an equivalent amount or, preferably a slight excess of a 1-3, preferably 1.5 to 2.5, molar solution of an alkali metal bicarbonate, the solution having been heated to 50°-100° C., preferably 80°-100° C. The alkali metal bicarbonate is advantageously used in an excess of up to 20, preferably from 0.5 to 3, % by weight, based on the theoretical amount of bicarbonate. After the metal salt solution has been added, stirring is advantageously carried out for a further 10-30, preferably 15-20 minutes, and the resulting precipitate is then filtered off, washed with water and dried at from 50° to 200° C., preferably from 100° to 160° C. A particularly suitable alkali metal bicarbonate is sodium bicarbonate. However, it is also possible to use ammonium bicarbonate for the precipitation. Mixtures of the stated bicarbonates may also be used. Furthermore, it is possible to effect precipitation of the metal ions using solutions of alkali metal carbonates e.g. sodium carbonate and/or potassium carbonate, if carbon dioxide is passed into the initially taken alkali metal carbonate solution during the precipitation; this amounts in the end to precipitation with bicarbonate.

Calcination is advantageously carried out at from 250° to 400° C., for example for from 5 to 40, in particular from 15 to 30, hours. Before the catalyst is actually used, it is reduced with hydrogen, advantageously at from 180° to 500° C., preferably from 250° to 450° C., for example in the course of from 5 to 100, advantageously from 10 to 25, hours.

During the hydrogenation, a residence time of from 1 to 120 minutes is advantageously maintained. Furthermore, a space velocity of from 0.2 to 2 kg of 5formylvalerate per liter of catalyst per hour has proven useful.

The reaction can be carried out batchwise, for example in a pressure vessel, or continuously in a reaction zone containing a fixed bed catalyst, by the liquid phase or trickle bed procedure. It has proven particularly useful to avoid back-mixing during the reaction.

In a third stage (stage c), the 6-aminocaproic acid obtained in stage b is cyclized to give caprolactam. Advantageously, the 6-aminocaproic acid solution obtained in stage 3 is used. For this purpose, and where the hydrogenation is carried out by the suspension method, the catalyst is first separated off. This can be effected, for example, by filtration or centrifuging. The ammonia is removed, prior to cyclization, from the resulting ammoniacal solution of aminocaproic acid in an inert solvent. This can be done, for example, by distilling off the ammonia from the aminocaproic acid solution. If this were not done, the yields of caprolactam obtained in the cyclization would be lower than those obtained in the absence of ammonia. Preferably, the content of ammonia in the starting solution is maintained at <1, in particular <0.5, % by weight.

The cyclization of the 6-aminocaproic acid is preferably carried out in the same solvent as that used for the hydrogenation, water or alkanols of 1° to 5 carbon atoms being preferred. However, it is also possible to replace the solvent used in the hydrogenation by another solvent.

Solutions which contain from 1 to 20, in particular from 2 to 10, % by weight of 6-aminocaproic acid are advantageously used for the cyclization. The reaction is carried out at from 150° to 370° C., in particular from 250° to 330° C., in general under the autogenous pressure of the reaction mixture, for example from 5 to 400 bar, batchwise or continuously, for example in a tube reactor. The mean residence times are from 0.2 to 2 hours.

The caprolactam formed is preferably isolated by extraction, for example using an extracting agent such as methylene chloride, chloroform, cyclohexane, toluene, benzene or trichloroethylene.

The Examples which follow illustrate the process according to the invention.

EXAMPLE 1

36 g of methyl 5-formylvalerate, 90 g of water and 0.5 g of sulfuric acid were refluxed for 3.5 hours, the methanol formed being distilled off constantly. Fractional distillation under reduced pressure gave 18.5 g (yield 57% of theory) of 5-formylvaleric acid of boiling point 106°-112° C./1 mbar. $^{13}C$ NMR spectrum in D-chloroform: chemical shifts relative to tetramethyl silane as internal standard=21, 24, 34 and 44 ppm (4 methylene groups), 178 ppm (formyl group) and 203 ppm (carboxyl group).

EXAMPLE 2

36 g of methyl 5-formylvalerate, 90 g of water and 1 g of p-toluene sulfonic acid were refluxed for 8 hours, the methanol formed being distilled off constantly. Fractional distillation under reduced pressure gave 13.3 g (yield 41% of theory) of 5-formylvaleric acid.

EXAMPLE 3

36 g of methyl 5-formylvalerate, 90 g of water and 2 g of cation exchanger which consisted of crosslinked polystyrene containing sulfo groups were refluxed for 8.5 hours, the methanol formed being distilled off constantly. Fractional distillation under reduced pressure gave 24 g (74% of theory) of 5-formylvaleric acid.

EXAMPLE 4

Methyl 5-formylvalerate (5% FVE; 5–10 ml/h) and water (50–100 ml/h) were pumped continuously by the trickle bed procedure through two heatable steel tube reactors (internal temperature 60°-100° C.) which possessed a double jacket and were filled with a cation exchanger which consisted of crosslinked polystyrene possessing sulfo groups (reactor I: 100 ml of ion exchanger, no circulation; reactor II: 50 ml of ion exchanger, circulation of 0–30 l/h). The following amounts of 5-formylvaleric acid (5-FVA) and 5-FVE were determined in the reacted mixtures by gas chromatography:

| No. | Temp. (°C.) | Circulation reactor II (l/h) | 5-FVA (% by weight) | 5-FVE (% by weight) | Yield (% of theory) | Selectivity % |
|---|---|---|---|---|---|---|
| 4.1 | 60 | 15 | 10.39 | 1.89 | 78 | 89 |
| 4.2 | 80 | 15 | 6.36 | 0.59 | 78 | 84 |
| 4.3 | 100 | 15 | 4.00 | 0.38 | 53 | 56 |

Some of the reacted mixture (reaction temperature 60° C.) was subjected to fractional distillation under reduced pressure. The resulting yield of 5-FVA of boiling point 102°-123° C./1 mbar was 75% of theory.

The reacted mixtures were extracted with cyclohexane. After extraction, the following amounts of 5-FVA and 5-FVE were determined in the aqueous phases by gas chromatography:

| No. | 5-FVA (% by weight) | 5-FVE (% by weight) |
|---|---|---|
| 4.1 | 10.28 | 0.21 |
| 4.1 | 6.23 | 0.16 |
| 4.3 | 3.97 | 0.01 |

EXAMPLE 5

100 ml of 14.8% strength by weight 5-formylvaleric acid solution in water were pumped, at from 70° to 130° C. and under a hydrogen pressure of 150 bar, into a suspension of the catalyst in aqueous ammoniacal solution in a 300 ml stirred steel autoclave, after which stirring was carried out for 2 hours.

The aminocaproic acid in the reacted mixture was determined by quantitative HPLC chromatography.

| No. | Temp. (°C.) | Catalyst | Yield of 6-aminocaproic acid (% of theory) |
|---|---|---|---|
| 6.1 | 70 | 2g Raney nickel | 57 |
| 6.2 | 110 | 2g Raney cobalt | 57 |

| No. | Temp. (°C.) | Catalyst | Yield of 6-aminocaproic acid (% of theory) |
|---|---|---|---|
| 6.3 | 130 | 2g Raney nickel | 57 |

COMPARATIVE EXAMPLE 10 g of trimeric 5-formylvaleric acid, 60 g of 12.5% strength aqueous ammonia and 2 g of Raney nickel were stirred for 5 hours at 110° C. and under a hydrogen pressure of 150 bar in a 300 ml stirred steel autoclave. The yield of 6-aminocaproic acid in the reacted mixture was determined as 31% of theory by quantitative HPLC chromatography.

EXAMPLE 6

(a) 5-formylvaleric acid obtained by hydrolyzing methyl 5-formylvalerate

5–10 ml/h of 5-FVE and 50–100 ml/h of water were pumped continuously through two heatable steel tube reactors (internal temperature 60° C.) which had a double jacket and were filled with a strongly acidic ion exchanger. (Reactor I: no circulation; reactor II: circulation of 15 l/h.)

The following amounts of 5-FVA and 5-FVE were determined in the reacted mixture by gas chromatography:

| 5-FVA (% by weight) | 5-FVE (% by weight) | Yield (% of theory) | Selectivity (%) |
|---|---|---|---|
| 7.03 | 0.80 | 78 | 85 |

The reacted mixture was extracted with cyclohexane. After extraction, the following amounts of 5-FVA and 5-FVE were determined in the aqueous phase by gas chromatography:

| 5-FVA (% by weight) | 5-FVE (% by weight) |
|---|---|
| 6.23 | 0.04 |

(b) 6-aminocaproic acid obtained by hydrogenation of 5-formylvaleric acid under aminating conditions.

100 ml of 5-formylvaleric acid solution in water (6.23% by weight of 5-FVA; reacted mixture from a) after extraction of the unconverted ester with cyclohexane) were pumped, at 110° C. and under a hydrogen pressure of 150 bar, into a suspension of 10 g of an Ru/Zr catalyst, containing 0.5% by weight of Ru and 1% by weight of Zr on alumina, in 60 g of 12.5% strength aqueous ammonia in a 300 ml stirred steel autoclave, after which stirring was carried out for 2 hours at 110° C. After cooling, the catalyst was filtered off. The aminocaproic acid in the reacted mixture was determined by quantitative HPLC, a yield of 77% of theory being found.

(c) Caprolactam obtained by cyclization of 6-aminocaproic acid.

An ammonia/water mixture was stripped off from the reacted mixture from (b) in a rotary evaporator in such a way that an ammonia-free, 4.3% by weight 6-aminocaproic acid solution in water remained. 46.5 ml/hour of this solution were pumped at 300° C. through a tube reactor having a capacity of 46.5 ml. The reacted mixture (886 g) obtained after a reaction time of 19 hours was extracted with chloroform. After the chloroform had been evaporated off from the combined extracts, 31.1 g (95% of theory) of caprolactam were obtained.

EXAMPLE 7

A solution of 15 g of 6-aminocaproic acid in 135 g of methanol was heated at 220° C. for 3 hours in a stirred autoclave. After the mixture had been cooled and methanol and water stripped off in a rotary evaporator, HPLC showed that the reacted mixture contained 11.4 g (88% of theory) of caprolactam.

We claim:

1. A process for the preparation of ε-caprolactam, wherein
   (a) a 5-formylvalerate is reacted with water in the presence of an acidic agent at from 30° to 200° C.,
   (b) the 5-formylvaleric acid thus obtained is reacted with excess ammonia and hydrogen in the presence of a hydrogenation catalyst and of a solvent which is inert under the reaction conditions, at from 50° to 150° C. under superatmospheric pressure, and
   (c) after the ammonia has been separated off, the resulting solution of 6-aminocaproic acid is heated to 150°–370° C. and the caprolactam formed is isolated.

2. A process as claimed in claim 1, wherein from 50 to 150 moles of water are used per mole of 5-formylvalerate.

3. A process as claimed in claim 1, wherein from 0.002 to 0.25 mole of a nonoxidizing mineral acid, a Lewis acid or a sulfonic acid is used per mole of 5-formylvalerate.

4. A process as claimed in claim 1, wherein a strongly acidic cation exchanger is used.

5. A process as claimed in claim 1, wherein a 5-formylvalerate is passed with water through two reaction zones which are connected in series and charged with strongly acidic cation exchangers, the reaction mixture being circulated in the second reaction zone and the aqueous solution removed being extracted with a hydrocarbon.

6. A process as claimed in claim 1, wherein the aqueous 5-formylvaleric acid solution obtained from stage a is used in stage b.

7. A process as claimed in claim 1, wherein from 4 to 30 moles of ammonia are used per mole of 5-formylvaleric acid.

8. A process as claimed in claim 1, wherein the 6-aminocaproic acid solution obtained from stage b is used in stage c.

9. A process as claimed in claim 1, wherein a solution of 6-aminocaproic acid containing <1% by weight of ammonia is used in stage c.

* * * * *